United States Patent [19]
Bieniarz

[11] Patent Number: 6,045,500
[45] Date of Patent: Apr. 4, 2000

[54] FETAL MOVEMENT RECORDER INSTRUMENT

[76] Inventor: Andre Bieniarz, 175 E. Delaware Ave., Ste. 7902, Chicago, Ill. 60611

[21] Appl. No.: 08/979,510

[22] Filed: Nov. 26, 1997

Related U.S. Application Data

[60] Provisional application No. 60/031,819, Nov. 26, 1996.

[51] Int. Cl.[7] .................................................. A61N 5/00
[52] U.S. Cl. ........................ 600/300; 600/304; 600/351; 128/897
[58] Field of Search .................................. 600/300–301, 600/304, 313, 351, 376, 511; 128/898, 904, 905, 920–925, 897–899

[56] References Cited

U.S. PATENT DOCUMENTS

| | | | |
|---|---|---|---|
| 4,493,043 | 1/1985 | Forbath | 702/178 |
| 4,898,179 | 2/1990 | Sirota | 600/483 |

OTHER PUBLICATIONS

Jason C. Birnholz, John C. Stephens, and Michael Faria; Fetal Movement Patterns: A Possible Means of Defining Neurologic Development Milestones in Utero Am J Poentgenol vol. 130 pp. 537–540, Mar. 1978.

Adrian Grant, Lil Valentin, Diana Elbourne, Sophie Alexander; Routine Formal Fetal Movement Counting And Risk OF Antepartum Late Death In Normally Formed Singletons; The Lancet Saturday Aug. 12, 1989; pp. 345–349.

Timothy R.B. Johnson, MD, Elizabeth T. Jordan, RNC, MSN, and Lisa L. Paine, CNM, DrPH; Doppler Recordings of Fetal Movewment: II. Comparision With Maternal Perception; vol. 76, No. 1, Jul. 1990.

Leo R. Leader, MRCOG, Peter Baillie, FRCOG, and Dirk J. Van Schalywyk, PhD; Fetal Movements and Fetal Outcome: A Prospective Study vol. 57, No. 4, Apr. 1981.

Robert M. Liston, MB, Arnold W. Cohen, MD, Michael T. Mennuti, MD, and Steven G. Gabbe, MD; Antepartum Fetal Evaluation by Maternal Perception of Fetal Movement; vol. 60, No. 4, Oct. 1982.

Thomas R. Moore, MD, and Kathleen Piacquadio, MD; A prospective evaluation of fetal movement screening to reduce the incidence of antepartum fetal death Am. J. Obstet Gynecol., May 1989; pp. 1075–1080.

Steen Neldam; Fetal Movements As An Indicator Of Fetal Wellbeing The Lancet, Jun. 7, 1980 pp. 1222–1224.

Steen Neldam; Fetal Movements as an Indicator of Fetal Well–being Dan Med Bull 1983; vol. 30 pp. 274–280.

Steen Neldam; Fetal movements A comparison between maternal assessment and registration by means of dynamic ultrasound Dan Med Bulletin 1982; vol. 29 pp. 197–199.

James A. O'Leary, M.D. and George C. Andrinopoulos, M.D.; Correlation of daily fetal movement and the nonstress test as tools for assessment of fetal welfare Am. J. Obstet. Gynecol. Jan. 1, 1981 pp. 107–108.

James F. Pearson, Judity B. Weaver; Fetal activity and fetal wellbeing: an evaluation British Medical Journal, 1976, vol. 1, pp. 1305–1037 May 29.

Thomas R. Moore, MD, and Kathleen Piacquadio, MD; A prospective evaluation of fetal movement screening to reduce the incidence of antepartum fetal death Am. J. Obstet. Gynecol. May 1989 pp. 1075–1080.

(List continued on next page.)

*Primary Examiner*—Cary O'Connor
*Assistant Examiner*—Michael Astorino
*Attorney, Agent, or Firm*—Marshall, O'Toole, Gerstein, Murray & Borun

[57] ABSTRACT

A fetal movement recorder instrument for registering perceived fetal movement includes an actuator operated by the maternal patient to indicate a perceived fetal movement by the maternal patient, the relative intensity, date, and time, so as to provide a corresponding actuator output signal. A data log unit receives and records the perceived fetal movement information over a preset counting period. A start/stop count alarm provides a stop count indication when the preset counting period is over, and a display provides a message corresponding to the number of fetal movement counts over a predetermined time. The recorded information is transmitted from the data log/base station to the care provider's location where feedback information may be transmitted back to the base station at the maternal patient location.

20 Claims, 2 Drawing Sheets

OTHER PUBLICATIONS

William F. Rayburn, M.D.; Antepartum Fetal Assessment Monitoring Fetal Activity Clinics in Perinatology vol. 9, No. 2, Jun. 1982 pp. 231–252.

William F. Rayburn, M.D.; Clinical implications from monitoring fetal activity Am. J. Obstet. Gynecol. Dec. 15, 1982 pp. 967–980.

Eliahu Sadovsky, M.D., Haim Yaffe, M.D., and Wolfe Z. Polishuk, M.D.; Fetal Movement Monitoring in Normal and Pathologic Pregnancy vol. 12, No. 3, 1974 pp. 75–79.

Eliahu Sadovsky, MD and Wolfe Z. Polishuk, MD.; Fetal Movements in Utero Nature, Assessment, Prognostic Value, timing of Delivery vol. 50, No. 1, Jul. 1997 pp. 49–55.

Jennifer Westgate MB, ChB, Murray Jamieson FRNZCOG; Stillbirths and fetal movements NZ Med J 1986 vol. 99 pp. 116–119.

FETAL MOVEMENT RECORDER INSTRUMENT

This application is based on provisional application Ser. No. 60/031,819 filed Nov. 26, 1996.

This invention relates to fetal movement monitors and in particular to an instrument for recording and monitoring maternally perceived fetal movement.

BACKGROUND OF THE INVENTION

Fetal neuro-muscular activity is one of the basic physiological functions of the developing organism and is necessary for normal neural, muscular and skeletal development of the fetus. Fetoplacental unit dysfunction or severe impairment of nutrient supply by the maternal circulation are expected, and do, lead to decreased fetal neuro-muscular activity. Accordingly, it has long been recognized that there is a direct correlation between fetal movement and the health of the pregnancy, or in other words, the value of reduced fetal movement as a predictor of intrauterine fetal death.

This has led to the clinical use of fetal movement assessment in preventing fetal death and untoward pregnancy outcome, in both low and high risk pregnancies. For instance, in one study involving high risk pregnancies, women were asked to engage in fetal movement counting for at least one hour each day, and wherein a fetal movement count of three or less was considered abnormal. The predictive value for an unfavorable perinatal outcome with reduced fetal activity was similar to that of a nonreactive nonstress fetal heart test. The experience of fetal movement counting in high risk pregnancy has prompted the suggestion that fetal movement counting be applied as a means of fetal assessment to the general pregnant population. In certain studies, women counted fetal movements for one hour, two hours after a meal, three times weekly after 30 weeks gestation. Counts below three were repeated for a second hour, and women were instructed to report if the count remained at fewer than three per hour. When a reduction in fetal movement was perceived, further fetal evaluation, using ultrasound and antepartum heart rate monitoring, was instituted and delivery expedited if fetal movement remained reduced.

The results pointed toward a potential benefit of fetal movement counting in low risk pregnancy and with a low false-positive rate ranging from 1 to 8%. However, the rates of attrition reported for low risk patients assigned to a fetal movement counting protocol were higher than in high risk studies (30–50%). It is possible that patient motivation in a problem pregnancy may be higher as such patients are driven by concern about fetal condition, whereas low risk patients may regard any testing as "unnecessary intervention".

Maternal perception of fetal movement constitutes the most widely used method of fetal activity assessment in today's clinical practice.

The major drawback of this method of fetal activity assessment consists in the cumbersome tools presently used to record maternal perception of fetal activity. The cumbersome nature of maternal fetal movement counting process most probably represents the major reason for low patient compliance and low response to the alarm signals. Mothers can not be expected to record the time and intensity of all the fetal movements and usually record only the time at which the fetal movement counting started and the time when ten fetal movements were appreciated and the counting was thus discontinued. Recording the time of each perceived movement or the relative subjective strength of each movement is not possible without the assistance of a recording device which until now is not available. Comparison of the fetal movement patterns with previous records generated by the same mother and fetus pair is entirely impossible without the assistance of computer analysis. Assessment of patent's compliance with fetal movement counting or recording protocols can take place only at the time of prenatal visit. The day to day decision concerning adequacy of fetal activity is left to the patient who might doubt her ability to adequately assess the fetus and thus frequently ignores the warning and alarm criteria. Requiring the patient to interpret the record of fetal movement is not appropriate and has been amply demonstrated to be only partially effective.

Maternal compliance with any fetal movement counting protocol represents a major problem. Approximately only 80% of patients adhere to the counting protocol and only 40–60% of those counting report decreased fetal movements when required by the criteria set in their counting protocol. (2) Thus, fetal movement counting protocols are correctly exercised in only 50% of the patients participating in any fetal movement counting protocol. Thus, given the unreliability of the "measuring instrument", the mother, it is truly remarkable that great majority of the studies published to date clearly demonstrate clinical usefulness of fetal movement counting by the mother in preventing fetal death and compromise.

Maternally perceived fetal movement counting is undoubtedly beneficial. The difficulties encountered in implementing the different fetal movement counting protocols make the development of a device which would facilitate the recording of the maternally perceived fetal movement and standardize the interpretation of the movement record extremely important.

In spite of the apparent clinical importance of fetal movement in determining the well being of the pregnancy no instruments capable of recording maternally perceived fetal activity in non-invasive, unobtrusive, semi-quantitative, and partially objective fashion is presently commercially available.

SUMMARY OF THE INVENTION

In accordance with the principles of the present invention, there is provided an instrument which enables partially quantitative, non-invasive and unobtrusive registering of maternally perceived fetal activity. In addition this recorder instrument can transmit, daily, the maternally perceived fetal activity record to a central monitoring station for computer analysis, comparison with previously generated records by the same patient, and for assessment of the patients compliance with monitoring and the patient's response to decreased fetal activity.

In particular, the recording instrument has the following characteristics:

1. a portable data recorder unit—not larger than a large beeper;
2. provide an alarm to alert the patient, at three preset times, to the need for scheduled fetal movement counting;
3. record the date and time of the beginning and end of each fetal movement counting period;
4. record the date and time of each fetal movement during the counting period;
5. record the relative strength of each fetal movement on an intensity scale of 1–3;

6. provide an indication when a preset number of movements have been observed to inform the patient that she may now stop counting;
7. provide an alarm to the patient and display an appropriate message on a display panel if the following conditions are met:
   (a) a preset time to count a preset number of fetal movements (i.e. two hours to count ten movements) is exceeded;
   (b) the time to count a preset number of fetal movements is a preset percentage longer or shorter than average for this particular fetus; and
   (c) the number of fetal movements over a preset time period is a preset percentage longer or shorter than the average for this particular fetus;
8. daily communications from the recorder through for instance a phone line with a base station computer and downloading of the fetal movement monitoring data from the recorder to the computer;
9. the recorder unit can receive information from the base station computer such as updated variables which will trigger display messages and alarms on the recorder unit;
10. the base station computer can store the historical data of daily fetal movement and perform the required operations to analyze the fetal movement information;
11. the base station computer can identify the patients who fail to monitor the fetal movements within the last 24 hours and automatically generate a phone log for patient contact through an automatic dialer;
12. a similar identification and processing of information of patients who met the worrying or alarm criteria but did not call the care provider at the base station will be provided by the base station computer; and
13. contacting the patient is facilitated by a beeper-like function contained in the recorder unit.

BRIEF DESCRIPTION OF THE DRAWINGS

The features of this invention which are believed to be novel are set forth with particularity in the appended claims. The invention may be best understood by reference to the following description taken in conjunction with the accompanying drawings, in which like reference numerals identify like elements in the several figures and in which:

DETAILED DESCRIPTION

Figure 1:
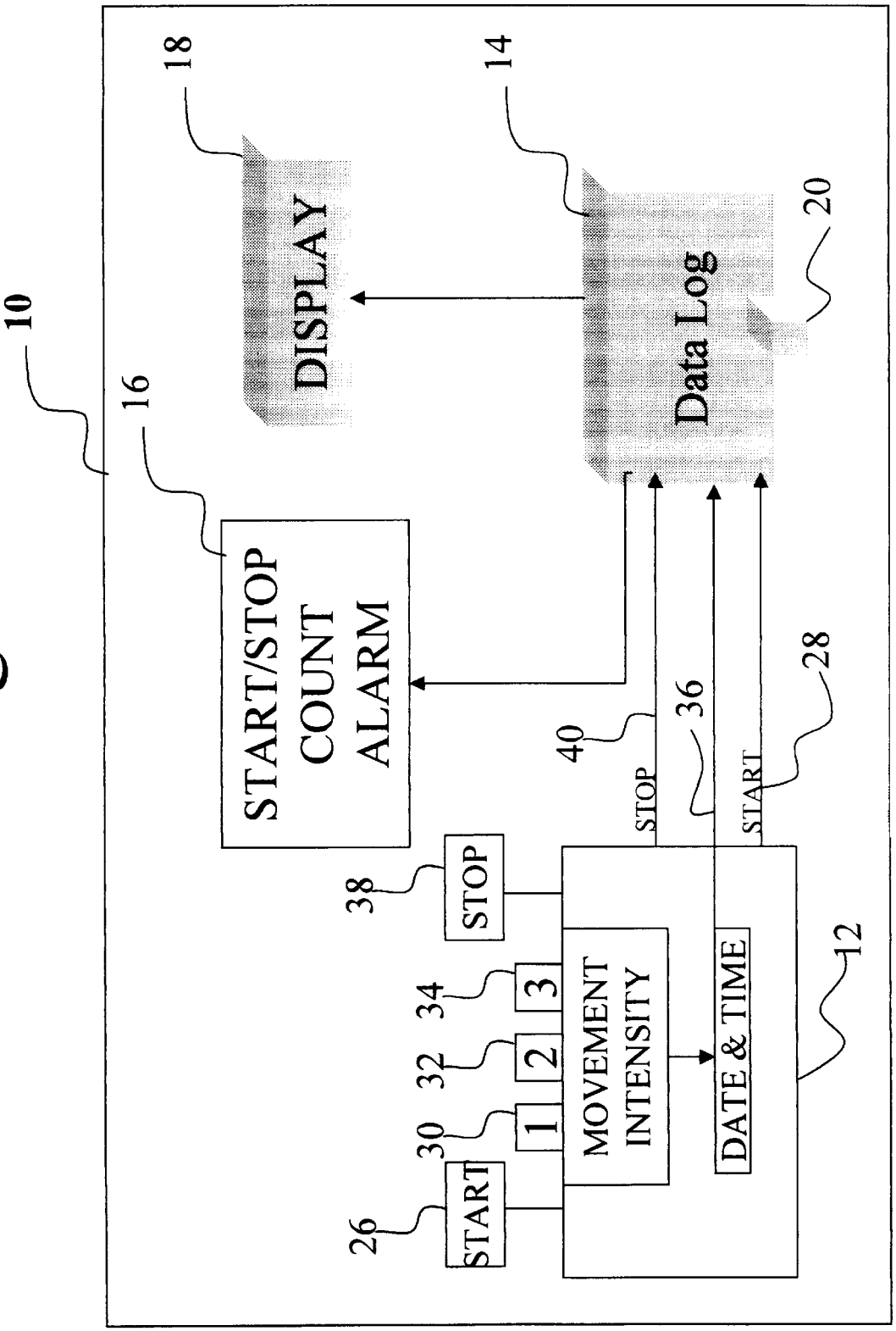
FIG. 1 is a schematic block diagram illustrating a fetal movement recorder instrument for maternally perceived fetal movement in accordance with the principles of the present invention.

Referring now to FIG. 1, there is illustrated a recorder instrument 10 which includes an actuator 12 through which a patient can register maternally perceived fetal movement, a data log unit 14 for recording the fetal movement information, an audio start/stop count alarm 16 and a display, such as an LCD display 18. The entire fetal movement recorder instrument 10 is portable and is not any larger than a large beeper, and includes a power and signal communication connector 20 for coupling into a base station unit 22 when the recorder is not being used for recording fetal movement.

Figure 2:
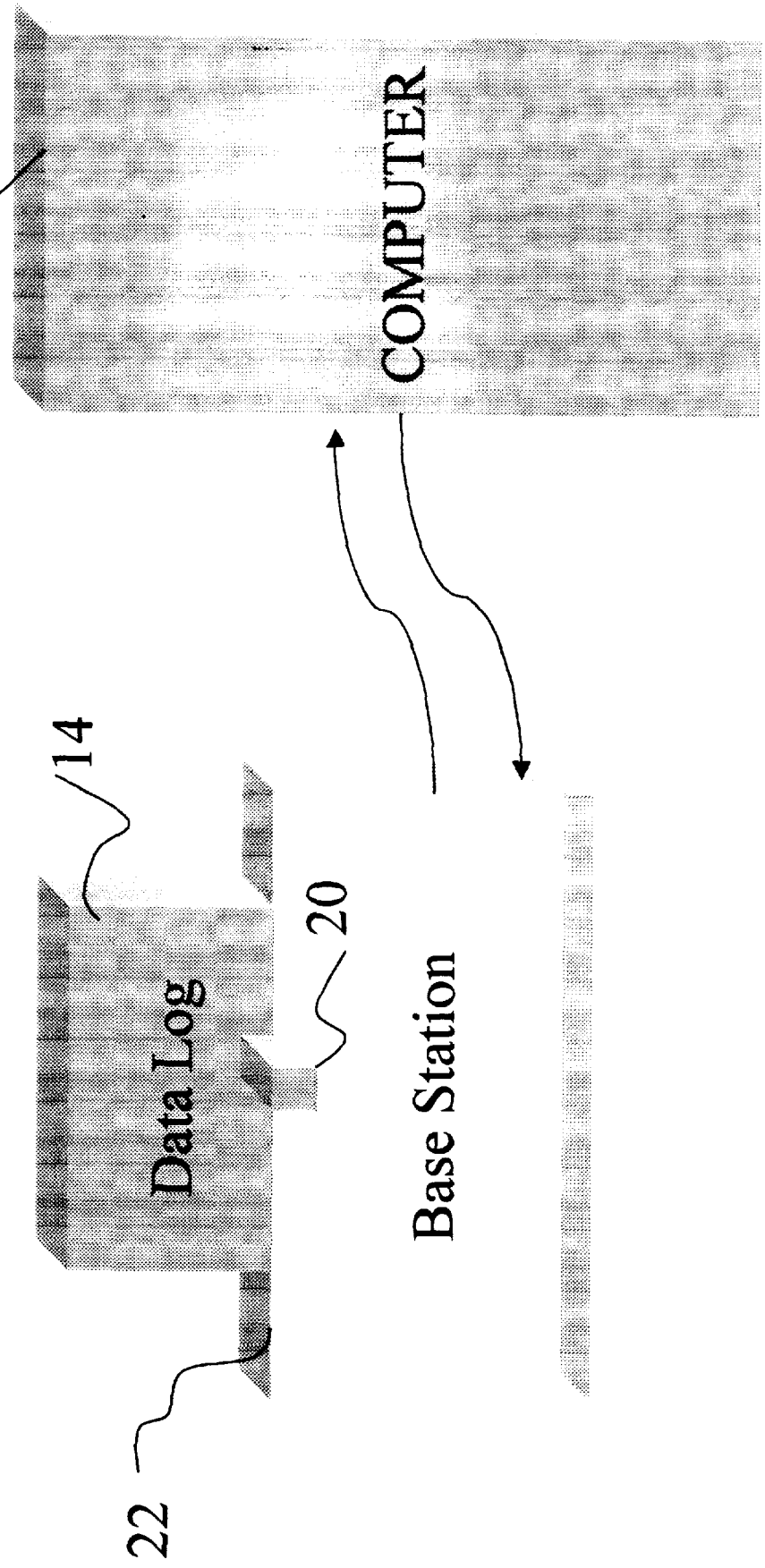
FIG. 2 is a schematic block diagram illustrating the transmitting of information from the recorder data logger via a base station to an off-site signal evaluation facility containing a computer and the transmitting of information from the computer to the base station.

As shown in FIG. 2, with the data log unit 14 coupled into the base station 22, the recorded fetal movement activity information can be transmitted to a computer 24 at the care providers facility. Such communication can be provided over the phone lines utilizing available data modems. Similarly, the computer 24 at the care providers facility can transmit information to the base station 22 as will be described more particularly hereinafter.

For convenience, only the data log unit 14 is illustrated in FIG. 2, it being understood that the entire fetal movement recorder instrument 10 containing the data log unit 14 is actually mounted onto the base station 22. The base station 22 can include a battery charger unit for charging a battery in the fetal movement recorder instrument 10.

When a patient is ready to record fetal movements, the portable recorder instrument 10 is removed from the base station 22 and the patient actuates a start button 26 which provides a signal on start line 28 to the data log unit 14 to record the date and time of the beginning of the fetal movement counting period. If the patient did not actuate the start button 26 at a preset time, the data log unit 14 provides a start count alarm on audio alarm unit 16 to alert the patient to the need for a scheduled fetal movement counting. It is preferred that the data log unit 14 can alert the patient at three preset times to the need for scheduled fetal movement counting.

The patient will now monitor fetal movement and provide an indication of a detected fetal movement by actuating one of the actuators 30, 32 or 34 depending on the perceived relative strength of the fetal movement on a 1 to 3 intensity scale. By actuating one of the actuators 30, 32 or 34, the patient not only notes the intensity of the fetal movement but also provides an indication of the date and time, all of which information is provided on line 36 to the data log unit 14. When a preset number of fetal movements have been observed and recorded in the data log unit 14, data log 14 provides a stop count signal to the audio alarm 16 to inform the patient that she may now stop fetal movement counting. The patient may then actuate stop button 38 to provide a corresponding stop signal on line 40, which information is recorded in the data log 14 to signal the end of this fetal movement counting period.

The data log 14 compares the total time for the just completed counting period to a preset time to count a preset number of fetal movements (i.e. two hours to count 10 movements) and provides an alarm on alarm unit 16 and an appropriate message on display 18 when this preset time is exceeded. In addition, the data log 14 also provides an alarm and displays an appropriate message if the time to count a preset number of movements is a preset percentage longer or shorter than the average for this particular fetus. Furthermore, the data log unit 14 also provides an alarm on unit 16 and an appropriate message on display 18 if the number of fetal movements over a preset time period during the last counting period is a preset percentage longer or shorter than the average for this particular fetus.

On a daily basis, the patient can mount the fetal movement recorder instrument 10 onto the base station 22 for transmitting the fetal movement monitoring data to the computer 24 at the care providers facility. The computer 24 stores the historical data of daily fetal movement and performs all of the desired operations to analyze the fetal movement information. Also, as appropriate, the computer 24 can transmit information on updated variables to the base station 22 and thereby into the data log 14 which updated information provides the basis for messages and alarms on the data log unit 14 as previously described.

If there are patients who have failed to monitor the fetal movements within the past 24 hours, the computer 24 identifies such patients and automatically generates a phone log for patient contact through an automatic dialer. Also, if there are patients who had been provided a warning or an alarm after a counting session, and such patients did not call the care provider, the computer 24 will identify and process such information. In this instance, contacting the patient can be facilitated by a beeper-like function which can be built into the recorder instrument 10.

Accordingly, the present invention provides the following features and advantages:

1. Easier more accurate more reliable and less cumbersome method of recording maternally perceived fetal movements;
2. Permanent record of each counting session;
3. Improved detection by allowing the mother to record even the very faint movements;
4. Exact timing of the movements;
5. Will allow analysis of frequency, pattern and intensity of maternally perceived fetal activity;
6. Will permit automatic electronic comparison of a fetal movement record with previously generated fetal movement records by the same patient;
7. Will expand the analytic possibilities by allowing within patient and between patients computer comparison of fetal movement records;
8. Will improve patient compliance with fetal movement monitoring protocols by alarms and daily feedback to the care provision site;
9. Will permit early detection of compliance problems which will allow for additional patient education and encouragement;
10. Will identify early those patients who are unable to dedicate the time for fetal monitoring and thus possibly are at significant risk of stress and of being unable to detect adequate time to the newborn in the post-partum period;
11. Will permit early identification of patients who are unwilling to participate in the care of their fetus;
12. Will provide the opportunity for early social intervention in noncompliant patients;
13. Will identify early those patients with compliance problems in responding to the warning and alarm signals of decreased fetal movement; and
14. Development of standardized antepartum fetal well being test based on maternal perception of fetal movement.

The foregoing detailed description has been given for clearness of understanding only, and no unnecessary limitations should be understood therefrom, as modifications will be obvious to those skilled in the art.

What is claimed is:

1. A fetal movement recorder instrument for registering perceived fetal movement by a maternal patient, said fetal movement recorder instrument comprising:

an actuator including means for the maternal patient to indicate a perceived fetal movement in an actuator output signal;

a data log unit coupled to the actuator and receiving the actuator output signal to record and store the actuator output signals, the data log unit further being adapted to compare the stored output signals to a predetermined value;

an alarm unit coupled to the data log unit and providing an indication when the predetermined value has been achieved; and a display coupled to the data log unit providing a display message indicative of the stored output signals.

2. A fetal movement recorder instrument according to claim 1, said actuator including means responsive to maternal input for indicating a relative intensity of the perceived fetal movement, and wherein the actuator is adapted to reflect the relative intensity in said actuator output signal.

3. A fetal movement recorder instrument according to claim 2, said actuator including means for indicating the date and time of the perceived fetal movement in said actuator output signal.

4. A fetal movement recorder instrument according to claim 3, including a base station for transmitting the stored output signals in said data log unit to a remote location.

5. A fetal movement recorder instrument according to claim 4, wherein said base station and data log unit include means for transferring the stored output signals in said data log unit to said base station.

6. A fetal movement recorder instrument according to claim 4, wherein said data log unit is adapted for connection to said base station for transferring the stored output signals in said data log unit to said base station.

7. A fetal movement recorder instrument according to claim 4, including means for receiving information at said base station communicated from said remote location.

8. A fetal monitor for use by a mother, comprising:

an actuator, the actuator being responsive to input by the mother and being adapted to register fetal movement information, the actuator further being adapted to generate one or more output signals indicative of the fetal movement information;

a data log unit operatively coupled to the actuator to thereby record the actuator output signals received during a predetermined time period;

an alarm unit operatively coupled to the data log unit, the alarm unit being adapted to provide a start and stop alarm to the mother indicating a proposed commencement and a proposed conclusion, respectively, of the predetermined time period; and a display operatively coupled to the data log unit, the display being adapted to convey selected fetal movement information from the data log unit to the mother.

9. The fetal monitor of claim 8, wherein the actuator is adapted to register fetal movement information indicative of the intensity perceived by the mother.

10. The fetal monitor of claim 8, wherein the actuator is adapted to signal to the data log unit an actual commencement and the actual conclusion of an predetermined time period in response to input by the mother.

11. The fetal monitor of claim 10, wherein the actuator is adapted to signal to the data log unit the date and time of each output signal.

12. The fetal monitor of claim 8, wherein the data log unit is adapted to compare the recorded output signals to target criteria.

13. The fetal monitor of claim 12, wherein the target criteria includes a target number of registered fetal movements during the predetermined time period.

14. The fetal monitor of claim 8, including a computer located at a remote facility, the data log unit being adapted to store the received output signals as historical data, the data log unit being further adapted for connection to a base station, the base station being adapted to transmit the historical data to the computer.

15. The fetal monitor of claim 14, wherein the computer is adapted to store target criteria and to compare the transmitted historical data to the target criteria.

16. The fetal monitor of claim 12, including a computer located at a remote facility, the data log unit being adapted to store the received output signals as historical data, the data log unit being further adapted for connection to a base station, the base station being adapted to transmit the historical data to the computer and the computer being adapted transmit the target criteria to the data log unit.

17. A fetal monitor for use by a pregnant mother at a location remote from a health care facility and without the intervention of health care personnel comprising:

an actuator, the actuator being adapted to register fetal movement perceived by the mother, the actuator further being adapted to generate a plurality of output signals indicative of the perceived fetal movement;

a data log unit operatively coupled to the actuator to thereby receive and record as actual data the actuator output signals, the data log unit being adapted to compare the actual data against predetermined target data;

an alarm unit operatively coupled to the data log unit, the alarm unit being adapted to signal the mother to commence and conclude a recording period; and a display operatively coupled to the data log unit, the display being adapted to transmit selected actual data from the data log unit to the mother.

18. The fetal monitor of claim 17, including a computer located at a remote facility, and wherein the data log unit is adapted for connection to a base station, the base station being adapted to transmit the actual data to the computer, the computer being adapted convey the target data to the data log unit.

19. The fetal monitor of claim 17, wherein the mother is physiologically equipped to perceive a relative intensity of the fetal movements, and wherein the actuator is adapted to permit the mother to input the relative intensity, the actuator further being adapted to generate output signals indicative of the relative intensity.

20. The fetal monitor of claim 17, wherein the target data includes a target number of fetal movements registered during a predetermined time period.

* * * * *